US00RE39592E

(19) United States
(12) Reissued Patent
Cady et al.

(10) Patent Number: US RE39,592 E
(45) Date of Reissued Patent: Apr. 24, 2007

(54) EXTENDED RELEASE GROWTH PROMOTING TWO COMPONENT COMPOSITION

(75) Inventors: Susan Mancini Cady, Yardley, PA (US); Claude Macar, Paris (FR); John W. Gibson, Springville, AL (US)

(73) Assignee: Intervet Inc., Boxmeer (NL)

(21) Appl. No.: 11/023,337

(22) Filed: Dec. 22, 2004

Related U.S. Patent Documents

Reissue of:
(64) Patent No.: 6,498,153
Issued: Dec. 24, 2002
Appl. No.: 09/273,862
Filed: Mar. 22, 1999

(30) Foreign Application Priority Data

Dec. 31, 1998 (FR) ..... 98 16707

(51) Int. Cl.
*A61K 31/56* (2006.01)
*A61K 31/335* (2006.01)
*C07J 1/00* (2006.01)
*C07D 313/08* (2006.01)

(52) U.S. Cl. ..... 514/170; 514/171; 514/178; 514/182; 514/450; 552/625; 552/646; 552/650; 549/269

(58) Field of Classification Search ..... 514/170, 514/171
See application file for complete search history.

(56) References Cited

U.S. PATENT DOCUMENTS

| | | | | |
|---|---|---|---|---|
| 2,232,438 | A | | 2/1941 | Butenandt |
| 2,236,574 | A | | 4/1941 | Koester et al. |
| 2,314,185 | A | | 3/1943 | Zondek et al. |
| 2,379,832 | A | | 7/1945 | Serini et al. |
| 3,239,345 | A | | 3/1966 | Hodge et al. |
| 3,248,294 | A | | 4/1966 | Nomine et al. |
| 3,773,919 | A | * | 11/1973 | Boswell et al. |
| 3,939,265 | A | * | 2/1976 | Grandadam |
| 4,166,800 | A | | 9/1979 | Fong |
| 4,192,870 | A | | 3/1980 | Grandadam et al. |
| 4,328,204 | A | | 5/1982 | Wasserman et al. |
| 4,331,651 | A | * | 5/1982 | Reul et al. |
| 4,351,337 | A | | 9/1982 | Sidman |
| 4,389,330 | A | | 6/1983 | Tice et al. |
| 4,393,041 | A | * | 7/1983 | Brown et al. |
| 4,450,150 | A | | 5/1984 | Sidman |
| 4,451,253 | A | | 5/1984 | Harman |
| 4,622,244 | A | | 11/1986 | Lapka et al. |
| 4,624,665 | A | * | 11/1986 | Nuwayser |
| 4,687,481 | A | | 8/1987 | Nuwayser |
| 4,758,435 | A | | 7/1988 | Schaaf |
| 4,834,978 | A | | 5/1989 | Nuwayser |
| 4,874,612 | A | | 10/1989 | Deasy |
| 4,876,093 | A | | 10/1989 | Theeuwes et al. |
| 4,900,735 | A | | 2/1990 | Grandadam |
| 4,902,515 | A | | 2/1990 | Loomis et al. |
| 4,927,687 | A | | 5/1990 | Nuwayser |
| 4,940,465 | A | | 7/1990 | Theeuwes et al. |
| 4,981,696 | A | | 1/1991 | Loomis et al. |
| 5,000,886 | A | | 3/1991 | Lawter et al. |
| 5,035,891 | A | | 7/1991 | Runkel et al. |
| 5,143,661 | A | | 9/1992 | Lawter et al. |
| 5,147,869 | A | | 9/1992 | Grandadam |
| 5,183,662 | A | | 2/1993 | Morita et al. |
| 5,211,952 | A | | 5/1993 | Spicer et al. |
| 5,288,496 | A | * | 2/1994 | Lewis |
| 5,340,584 | A | | 8/1994 | Spicer et al. |
| 5,340,585 | A | | 8/1994 | Pike et al. |
| 5,340,586 | A | | 8/1994 | Pike et al. |
| 5,366,734 | A | | 11/1994 | Hutchinson |
| 5,389,379 | A | * | 2/1995 | Dirix |
| 5,401,507 | A | | 3/1995 | Lewis |
| 5,407,609 | A | * | 4/1995 | Tice et al. |
| 5,419,910 | A | | 5/1995 | Lewis |
| 5,427,796 | A | | 6/1995 | Lewis |
| 5,434,146 | A | | 7/1995 | Labrie et al. |
| 5,518,730 | A | | 5/1996 | Fuisz |
| 5,534,250 | A | * | 7/1996 | Klaveness et al. |
| 5,534,263 | A | | 7/1996 | Wong et al. |
| 5,541,172 | A | | 7/1996 | Labrie et al. |
| 5,620,697 | A | | 4/1997 | Tormala et al. |
| 5,629,008 | A | * | 5/1997 | Lee |
| 5,629,303 | A | | 5/1997 | Labrie et al. |
| 5,633,002 | A | | 5/1997 | Stricker et al. |
| 5,643,595 | A | | 7/1997 | Lewis |
| 5,650,173 | A | | 7/1997 | Ramstack et al. |
| 5,654,008 | A | * | 8/1997 | Herbert et al. |
| 5,667,804 | A | | 9/1997 | Wong et al. |
| 5,686,092 | A | | 11/1997 | Lewis |

FOREIGN PATENT DOCUMENTS

| | | |
|---|---|---|
| DE | 37 10 175 A1 | 8/1988 |
| EP | 450 262 A1 | 12/1990 |
| EP | 257 369 B1 | 4/1992 |
| EP | 572 932 A2 | 5/1993 |
| GB | 2 167 662 A | 6/1986 |
| GB | 2 273 874 A | 6/1994 |
| WO | WO 94/15636 | 7/1994 |
| WO | WO 96/12466 | 5/1996 |

OTHER PUBLICATIONS

Deasy, P. et al., "Design and Evaluation of a Biodegradable Implant for Improved Delivery of Oestradiol–17β to Steers" (1993) International Journal of Pharmaceutics pp. 251–259.

Marcotte, N. et al.: "Delayed Release of Water–Soluble Macromolecules from Polylactide Pellets" (1989) Journal of Controlled Release, V9, pp. 75–85.

(Continued)

*Primary Examiner*—Barbara P. Badio
(74) *Attorney, Agent, or Firm*—Kenyon & Kenyon

(57) ABSTRACT

An extended release composition comprising a first composition comprising growth promoters and a second composition comprising growth promoters and a biodegradable polymer is described. A method of increasing weight gain in food animals utilizing the composition, a pharmaceutical dosage form containing the composition and a method of preparing the pharmaceutical dosage form are also described, as are pellets of the composition for implantation in food animals.

53 Claims, No Drawings

OTHER PUBLICATIONS

Foutz, C.P. et al. "Anabolic Implant Effects on Steer Performance, carcass Traits . . . " J. Animal Science (1997) V75, pp. 1256–1265.

Henricks, D.M., et al "Serum Concentrations of Trenbolone–17β and Estradiol–17β and Performance of Heifers Treated . . . " J. Animal Science (1997) V75 pp. 2627–2633.

Wuthrich, P. et al. "Pulsatile and delayed release of lysozyme from ointment–like polyl . . . " J. Controlled Release (1992) V21, pp. 191–200.

Asano, M, et al. "In vivo controlled release of a luteinizing hormone–releasing hormone agonist . . . " Intern. J. of Pharmaceutics (1997) V67, pp. 67–77, Netherlands.

Barnwell, S.G. et al. "Greatly enhanced oral bioavailability of propranolol using HALO liver by–pass drug deliver . . . " Journal of Controlled Release (1994) V28, pp. 306–309.

Mehta, R.C. et al. "Biogradable microspheres as depot system for parenteral delivery of peptide drugs" J. of Controlled Release (1994) V29, pp. 375, U.S.A.

Ryden, L. et al. "Dextran microspheres as a nasal delivery system for insulin in rats" (1994) Journal of Controlled Release (1994) 29, pp. 394 U.S.A.

Jones, R. et al "In vitro and in vivo release of metroclopramide from a subdermal diffusion matrix . . . " Journal of Controlled Release (1994) V30, pp. 35–44 U.S.A.

Macvinish, L.J., et al "The Effect of Implantation of Trenbolone Acetate and oestradiol17β in Wether Lambs . . . " Animal Products (1988) V47, p. 75–85, GB.

Hanes, J. et al. "Degradation and Erosion of Tyrosene–Containing Polyahydrides . . . " Proceedings of the Internat. Symp. on Controlled Release of Bioactive Materials (1994) 21,44.

Veronese et al. "Improved Enzyme Delivery By Surface Modification with Poly(vinylpyrrolidone) Oligomers" (1994) Proceedings of the Internat. Symp. on Controlled Release 21 298.

Gibson, J.W., et al. "Development of a Fibrous IUD Delivery System for Estradiol/Progesterone" Proceedings of an Internat. Workshop on Intrauterine Contraception . . . (1984) USA.

Ogawa, Y., et al. "In Vivo Release Profiles of Leuprolide Acetate from Microcapsules Prepared with Polylactic . . . " Chemical and Pharmaceutical Bulletin (1988) 36, 2576, Japan.

Preston, R.L. "Comparative Effectiveness of Somatotropin and Anabolic Steriods in Feedlot Steers" J. of Animal Science (1995) V23, p. 1038–1047.

Sandow, J. et al. "Pharmacokinetics and Endocrine Effects of Slow Release Formulations of LHRH . . . " J. of Steriod Biochemistry and Molecular Biology, V37, N36, p. 925–931, GB 1990.

Shah, N.H. et al "A biodegradable injectable implant for delivering micro and macromolecules . . . " (1993) Netherlands.

Hwang, Ruey–ching et al. "Effect of Binder and Geometry of Tablet on Rate of Wear, Hardness and Tensile Strength" Drug Develop. and Industrial Pharmacy (1993) 19(5), 507–519.

Lewis, D. "Controlled Release Micrspheres Technology" (1995) Acad. of Veterinary Consultants, V23, p. 51.

* cited by examiner

EXTENDED RELEASE GROWTH PROMOTING TWO COMPONENT COMPOSITION

Matter enclosed in heavy brackets [ ] appears in the original patent but forms no part of this reissue specification; matter printed in italics indicates the additions made by reissue.

Sustained release pharmaceutical composition containing growth promoters for use in food animals are described in U.S. Pat. No. 3,939,265 issued to J. A. Grandadam on Feb. 17, 1976 and U.S. Pat. No. 5,288,496 issued to D. H. Lewis on Feb. 22, 1994. The rate of release of the growth promoters of these compositions, however, generally does not comport with the growth periods of food animals in feedlots, the rate of release of the promoters declining over the growth period and becoming markedly reduced before the expiration of the period. To overcome this deficiency in feedlot growth promotion, it would be desirable to provide an extended release composition, from which the growth promoters are uniformly released over the growth period of the food animal in the feedlot, thereby enhancing the weight gain of the animal and improving the feed efficiency of the formulation. It has now been found that a composition comprising a first composition comprising growth promoters and a second composition comprising growth promoters and a biodegradable polymer releases the promoters over an extended period of time corresponding to the growth period of feedlot animals.

The present invention relates to an extended release composition comprising a first composition comprising growth promoters and a second composition comprising growth promoters and a biodegradable polymer. More specifically, the present invention relates to a composition comprising a first composition comprising a compound of formula 1

1

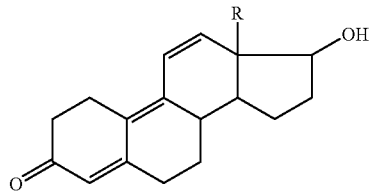

wherein R is loweralkyl; the ester derivatives, geometric isomers, stereoisomers, or optical isomers thereof, a compound of formula 2

2

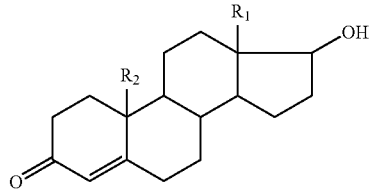

wherein $R_1$, and $R_2$ are loweralkyl; the ester derivatives, geometric isomers, stereoisomers, or optical isomers thereof, a compound of formula 3

3

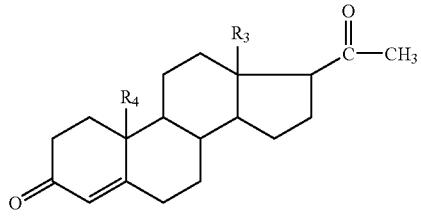

wherein $R_3$ and $R_4$ are loweralkyl; the geometric isomers, stereoisomers, or optical isomers thereof, a compound of formula 4

4

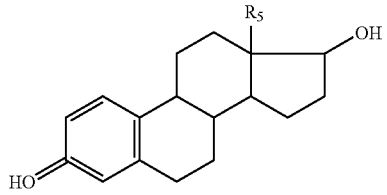

wherein $R_5$ is loweralkyl; the ester derivatives, geometric isomers, stereoisomers, or optical isomers thereof; or a compound of formula 5

5

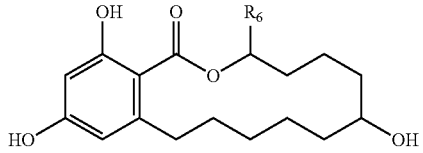

wherein $R_6$ is loweralkyl; the ester derivatives, geometric isomers, stereoisomers, or optical isomers thereof; and a second composition comprising a compound of formula 1

1

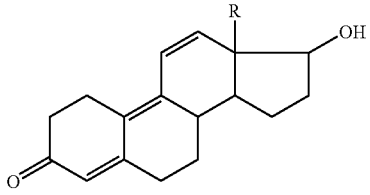

wherein R is loweralky; the ester derivatives, geometric isomers, stereoisomers, or optical isomers thereof, a compound of formula 2

2

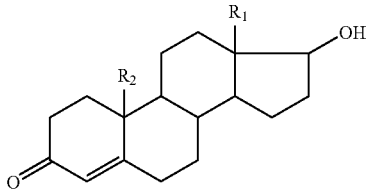

wherein $R_1$ and $R_2$ are loweralkyl; the ester derivatives, geometric isomers, stereoisomers, or optical isomers thereof, a compound of formula 3

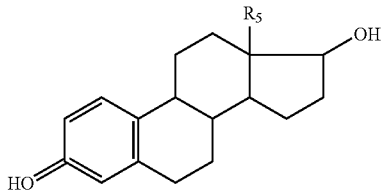

wherein $R_5$ is loweralkyl; the ester derivatives, geometric isomers, stereoisomers, or optical isomer thereof, a compound of formula 4

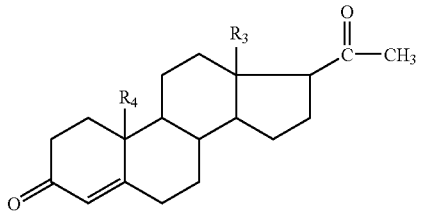

wherein $R_3$ and $R_4$ are loweralkyl; the geometric isomers, stereoisomers, or optical isomers thereof, and a compound of formula 5

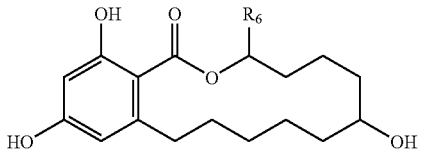

wherein $R_6$ is loweralkyl; the ester derivatives, geometric isomers, stereoisomers, or optical isomers thereof; and a biodegradable polymer selected from the group consisting of homopolymers and copolymers of γ-butyrolactone, δ-valerolactone, ϵ-caprolactone, glycolide, DL-lactide, L-lactide, glycolic acid, DL-lactic acid, L-lactic acid, and combinations thereof, polydioxanones, polyorthesters, polyanhydrides, polycarbonates, polyesteramides, and polyphosphazines, useful for the promotion of weight gain in food animals. The present invention also relates to a pharmaceutical dosage form containing the composition, a method of preparing the dosage form utilizing the composition, as well as pellets of the composition for implantation in food animals.

Preferred compositions of growth promoters are those wherein R, $R_1$, $R_2$, $R_3$, and R4, $R_5$ and $R_6$ are methyl and the aroyl or alkanoyl ester derivatives thereof, where applicable.

More preferred compositions are those wherein the growth promoters are;

(a) 17β-acetoxyestra-4,9,11-trien-3-one;

(b) 17β-benzoyloxyestra-4,9,11-trien-3-one;

(c) 17β-propionyloxy-4-androsten-3-one;

(d) pregn-4-en-3,20-dione;

(e) estra-1,3,5(10)-trien-3,17β-diol;

(f) 17β-benzoyloxyestra-1,3,5(10)-trien-3-ol;

(g) 3,4,5,6,9,10,11,12-decahydro-7,14,16-trihydroxy-3-methyl-1H(2)-benzoxacyclotetradecin 1-one.

Preferred biodegradable polymers are homopolymers and copolymers of glycolide, DL-lactide, L-lactide, glycolic acid, DL-lactic acid and L-lactic acid and combinations thereof.

More preferred biodegradable polymers are copolymers of DL-lactide and glycolide, copolymers of L-lactide and glycolide, polymers of L-lactide and polymers of DL-lactide, designated polylactides.

As used throughout the specification and appended claims, the term "alkyl" refers to a straight or branched chain hydrocarbon radical containing no unsaturation and having 1 to 5 carbon atoms. Examples of alkyl groups are methyl, ethyl, 1-propyl, 2-propyl, 1-butyl, 2-butyl, 1-pentyl, 3-pentyl, and the like; the term "alkanoic acid" refers to a compound formed by combination of a carboxyl group and a hydrogen atom or alkyl group. Examples of alkanoic acid are formic acid, acetic acid, propanoic acid, 1-methylpropanoic acid, 2,2-dimethylacetic acid, pentanoic acid, and the like; the term "alkanoyl" refers to the radical formed by removal of the hydroxyl group from an alkanoic acid. Examples of alkanoyl groups are formyl, acetyl, propanoyl, 2-methylpropanoyl, 2,2-dimethylacetyl, pentanoyl, and the like. The term "aryl" refers to an unsubstituted or a substituted phenyl group. Examples of aryl groups are benzene, 2-methylbenzene, 3-chlorobenzene, 4-hydroxybenzene, 3-methoxybenzene, methoxybenzene, 3-nitrobenzene, 2-trifluorobenzene, and the like. The term "aroic acid" refers to a compound formed by combination of an carboxyl group with an aryl group. Examples of aroic acids are benzoic acid, 2-methylbenzoic acid, 3-chlorobenzoic acid, 4-hydroxybenzoic acid, 3-methoxybenzoic acid, 3-nitrobenzoic acid, 2-trifluorobenzoic acid, and the like. The term "aroyl" refers to the radical formed by removal of the hydroxyl group from an aroic acid. Examples of aroyl are benzoyl, 2-methylbenzoyl, 3-chlorobenzoyl, 4-hydroxybenzoyl, 3-methoxybenzyol, 2-nitrobenzoyl, 2-trifluoromethylbenzoyl, and the like. The term "lower" as applied to any of the aforementioned groups or compounds refers to a group or compound having a carbon skeleton containing up to and including 5 carbon atoms. The expression "ester derivatives" refers to esters of the hydroxy group or groups of compounds of the present invention and an alkanoyl or aroyl group. Examples of ester derivatives are esters of formic acid, acetic acid, propanoic acid, 1-methylpropanoic acid, 2,2-dimethylacetic acid, pentanoic acid, benzoic acid, 2-methylbenzoic acid, 3-chlorobenzoic acid, 4-hydroxybenzoic acid, 3-methoxybenzoic acid, 2-nitrobenzoic acid and 2-trifluoromethylbenzoic acid and the like.

The compounds of the compositions of the present invention which lack an element of symmetry exist as optical antipodes and as the racemic forms thereof. The optical antipodes may be prepared from the corresponding racemic forms by standard optical resolution techniques or by synthesis from optically active precursors.

The present invention comprehends all optical isomers and racemic forms thereof and all stereoisomers of the compounds of the compositions disclosed and claimed herein. The formulas of the compounds shown herein are intended to encompass all possible optical and stereoisomers of the compounds so depicted.

The expression "food animal" refers to an animal raised for the purpose of providing a source of protein in the diet of humans or other animals. Examples of food animals are bovine animals, such as cows, cattle, steers, calves, and the like, ovine animals such as sheep; porcine animals such as pigs, and the like and avians such as chickens, turkeys and the like.

The expression "conventional drug delivery" refers to the temporally uncontrolled release of a drug into the blood of an animal resulting in a short duration of action, the blood levels of the drug being either initially high (intravenous administration) and falling off rapidly, or initially low (extramuscular administration), rapidly rising and falling off rapidly.

The expression "sustained release" refers to the slow release of a drug into the blood of an animal over a prolonged period of time wherein the blood levels of the drug decline rapidly over time, but not as rapidly as in conventional release.

The expression "controlled release" refers to sustained release wherein constant blood levels of the drug are maintained over a period of time.

The expression "delayed release" refers to the release of a drug into the blood of an animal after an induction period subsequent to the administration of the drug, without an initial burst release of the drug.

The expression "extended release" refers to the controlled release of a drug into the blood of an animal over a long period of time.

The expression "steroid" refers to a compound characterized by the presence of a perhydrocyclopentenophenanthrene ring system.

The term "biodegradable polymer" refers to those synthetic and naturally occurring water-insoluble polymers that degrade by hydrolysis or enzymatic processes. Examples of useful biodegradable polymers include, but are not limited to the aliphatic polyesters of hydroxy acids (i.e. the "polylactides") such as the homopolymers and copolymers prepared by ring-opening polymerization of glycolide, DL-lactide, L-lactide, γ-butyrolactone, δ-valerolactone, ϵ-caprolactone, as well as blends of these polymers. Other examples include homopolymers and copolymers prepared by directed condensation of glycolic acide, DL-lactic acid, L-lactic acid, and various other classes of polymers including the polydioxanones, polyorthoesters, polyanhydrides, polycarbonates, polyesteramides, polyamides and polyphosphazines.

The growth promoters of the compositions of the present invention are described in the art. For example, the steroids of the formulas 1 and 3 are described in U.S. Pat. No. 3,939,265 issued to J. A. Grandadam on Feb. 17, 1996; the steroids in formula 2 are described in U.S. Pat. No. 2,236,574 issued to H. Koester, et al., on Apr. 11, 1941; the steroid of formula 3 is described in U.S. Pat. No. 2,232,438 issued to A. Butendant on Feb. 18, 1941; and the macrocycles of formula 5 are described in U.S. Pat. No. 3,239,345 issued to E. B. Hodge, et al., on Mar. 8, 1966. The ester derivatives of the growth promoters are also described in the art, or may be prepared by conventional esterification techniques, e.g. treating compounds containing a hydroxyl group with an alkanoyl or an aroyl halide in the presence of an acid acceptor.

The "polylactides" as defined herein are described in U.S. Pat. No. 5,366,734 issued Nov. 22, 1994 to F. G. Hutchinson and are prepared by polymerization of lactic acid or glycolic acid, alone, or the corresponding lactides or glycolides, or copolymerization of lactic acid and glycolic acid, or the corresponding lactides and glycolides, as described therein, or are available from commercial sources, for example, Birmingham Polymers, Inc., Birmingham, Ala.

The biodegradable polymers of the compositions of the present invention, i.e. the polydioxanones, polyorthoesters, polyanhydrides, polycarbonates, polyesteramides, polyamides and polyphosphazines, are described in, for example, U.S. Pat. No. 5,508,730 issued to R. C. Fuissz on May 21, 1996, among others.

The extended release composition of the present invention comprises a first and second composition formulated as a pharmaceutical dosage form for administration to a food animal for weight gain in the feedlot. The first composition of the formulation comprises growth promoters of formulas 1 to 5 wherein R, $R_1$, $R_2$, $R_3$, $R_4$, $R_5$, and $R_6$ are as defined herein, and the ester derivatives thereof, preferably those growth promoters wherein R, $R_1$, $R_2$, $R_3$, $R_4$, $R_5$, and $R_6$ are methyl and the aroyl or alkanoyl ester derivatives thereof, where applicable, more preferably, growth promoters selected from the group consisting of:

(a) 17β-acetoxyestra-4,9,11-trien-3-one;

(b) 17β-benzoyloxyestra-4,9,11-trien-3-one;

(c) 17β-propionyloxy-4-androsten-3-one;

(d) pregn-4-en-3,20-dione;

(e) estra-1,3,5(10)-trien-3,17β-diol;

(f) 17β-benzoyloxyestra-1,3,5(10)-trien-3-ol; and (g) 3,4,5,6,9,10,11,12-decahydro-7,14,16-trihydroxy-3-methyl-1H(2)-benzoxacyclotetradecin-1-one.

The second composition of the formulation comprises growth promoters of formulas 1 to 5 wherein R, $R_1$, $R_2$, $R_3$, $R_4$, $R_5$, and $R_6$ are as defined herein and the ester derivatives thereof, preferably, those growth promoters wherein R, $R_1$, $R_2$, $R_3$, $R_4$, $R_5$, and $R_6$ are methyl and the aroyl or alkanoyl derivatives thereof, where applicable, more preferably, growth promoters selected from the group consisting of:

(a) 17β-acetoxyestra-4,9,11-trien-3-one;

(b) 17β-benzoyloxyestra-4,9,11-trien-3-one;

(c) 17β-propionyloxy-4-androsten-3-one;

(d) pregn-4-en-3,20-dione;

(e) estra-1,3,5,(10)-trien-3,17β-diol;

(f) 17β-benzoyloxyestra-1,3,5(10)-trien-3-ol;

(g) 3,4,5,6,9,10,11,12-decahydro-7,14,16-trihydroxy-3-methyl-1H(2)-benzoxacyclotetradecin-1-one, and a biodegradable polymer, preferably, homopolymers and copolymers of glycolide, DL-lactide, L-lactide, glycolic acid, DL-lactic acid and L-lactic acid, and combinations thereof, more preferably copolymers of DL-lactide and glycolide and copolymers of L-lactide and glycolide.

The formulation may contain, in addition to the growth promoters, the active ingredients, excipients, e.g., pharmaceutical binders and fillers, such as starch, ethylcellulose, cellulose acetate, sucrose, and polyvinylpyrrolidone. Ethylcellulose is preferred. The formulation may also contain an adhesive, for example, cholesterol, and a lubricant, for example, magnesium stearate.

The homopolymers and copolymers of glycolide, DL-lactide and L-lactide, glycolic acid, DL-lactic acid and L-lactic acid, and combinations thereof, are characterized by their composition and molecular weight. Composition can be conveniently determined by nuclear magnetic resonance spectrometry. For polymers prepared by ring-opening polymerization, the composition is described as the molar composition based on the cyclic monomers from which the polymer was prepared. For those prepared by direct condensation, the composition is described as the molar composition of the hydroxyacid residues present. The compositions of the polylactides that are useful in preparing the formulations described herein include all homopolymers and copolymers that exhibit glass transition or crystalline melting transition temperatures greater than about 40° C. The preferred compositions are those copolymers of DL-lactide and glycolide with monomer ratios in the range from about 50:50 to about 90:10 and the most preferred compositions are those with monomer ratios in the range from about 60:40 to about 75:25. All monomer ratios are expressed as the ratio of DL-lactide to glycolide Molecular weight can be monitored by dilute-solution viscosity measurements. As described herein, dilute-solution viscosities are measured in either chloroform (≧65% lactide) or hexafluroisopropanol (<65% lactide) at 30° C. and a concentration of about 0.5 g/dL (IV<1.5 dL/g) or 0.2 g/dL (IV=1.5–3.5 dL/g). The inherent viscosities of the polylactides may fall within the range of about 0.1 dL/g to about 3.5 dL/g; that of the preferred polymers being in the range of about 0.3 dL/g to about 1.5 dL/g.

The biodegradable polymer, preferably, a polylactide, of the second composition of the formulation serves as a coating of a core of the formulation and may be present as a minor component of the core in an amount within the range of from about 0 to about 10%.

The timing of the initial release of the growth promoters from the second composition formulation, the coated composition, is determined by the relative amounts of the promoters to the biodegradable polymeric coating, as well as the characteristics of the coating. Generally, the greater the proportion of biodegradable polymer to the growth promoters, the greater the retardation of the initial release of the growth promoters, i.e., the longer delayed release period. For example, in table 1, the uncoated pellet began releasing immediately while the 10.8 wt. % coasted pellet did not begin to release until approximately 45 days and the 19.8 wt. % of coated pellet did not begin to release until approximately 55 days.

The timing of release of the growth promoters from the coated formulation is also dependent on the relative proportions of the DL-lactide to glycolide units in the copolymers and the molecular weight thereof. Generally, the greater the proportion of DL-lactide units to glycolide units in the copolymer, the greater the delay of the release of the growth promoters from the formulation. For example, the delay of release of the growth promoters, 17β,-acetoxyestra-4,9,11-trien-3-one and estra-1,3,5(10)-trien-3,17β-diol, from the coated formulation decreased by increasing the amount of DL-lactide units in the copolymer in a formulation having a coating of DL-lactide-glycolide copolymer.

Generally, the greater the molecular weight of the biodegradable polymer, the greater the delay of the release of the growth promoters.

The in vitro rates of release of the growth promoters of the present invention are determined by conventional methods known in the art, for example, by the methods described by J. W. Gibson in Intrauterine Contraception: Advances and Future Prospects, G. I. Zatuchni, et al. Editors, Harper and Row, Philadelphia, Pa., 1984, pages 218 and 219. In one such in vitro method, for example, the second composition formulation containing growth promoters of formula 1 and 4, in the form of a coated pellet was added to an aqueous solution of a dissolution medium of sodium dodecyl sulfate (5 wt. %) and incubated at 37° C. Samples of the dissolution medium were removed periodically and analyzed by high performance liquid chromatography for the presence of the growth promoters.

The first composition of the present extended release composition is formulated by processes comprising operations conventional in the pharmaceutical arts. In a typical process, a mixture of growth promoters and excipients if any, namely, a binder and an adhesive, are combined in a high shear mixer, and the mixture is wetted with a granulated solution. The granulation is then screened, dried, a lubricant is added, and tableted into pellets.

The second composition of the extended release composition is formulated by mixing the growth promoters, excipients, if any, such as a binder and an adhesive, and a solution of a biodegradable polymer, evaporating the solution, screening and drying the granulate, adding a lubricant, and tableting the granulate. The tablets, so obtained, containing the biodegradable polymer in the core, are then coated with a solution of a biodegradable polymer to provide the coated delayed release pellets.

In practice, as detailed in the examples, a solution of a biodegradable polymer e.g. a polylactide, preferably a copolymer of DL-lactide and glycolide, characterized by its inherent viscosity, and having a ratio of lactide units to glycolide units, preferably in the range of from about 50:50 to 90:10, most preferably in the range from about 60:40 to about 75:25, is added to a granulation of growth promoters, such as, for example, 17β-acetoxyestra-4,9,11-trien-3-one, and estra-1,3,5(10)-trien-3,17β-diol, an adhesive, preferably, cholesterol, a binder, preferably, ethylcellulose, in a planetary mixer, and the solvent is evaporated. The dried granules are mixed with a lubricant, preferably magnesium stearate, then tableted with a press optimally equipped with tools having a beveled edge, the fill weight being from about 25 mg to about 50 mg, a fill weight of about 33 mg being preferred, to provide core tablets. A solution of a biodegradable polymer, preferably a copolymer having a ratio of DL-lactide to glycolide units of about 50:50 to about 90:10, most preferably in the range of from about 60:40 to about 75:25 in an organic solvent such as acetone is sprayed onto the core tablets in an air suspension coater-drier to provide delayed release pellets having the desired release rate properties.

The pellets of the first composition granulation, the uncoated sustained release pellets containing growth promoters and excipients, if any, and the second composition granulation, the delayed release pellets, containing growth promoters, a biodegradable polymer, preferably a polylactide and excipients, if any, coated with a biodegradable polymer, preferably a polylactide, are administered to food animals in the feedlot to afford extended release of the growth promoters over the feedlot period. The extended release of the growth promoters is a composite of the sustained release and delayed release characteristics of the uncoated first and coated second compositions, respectively. The rate of release of the sustained release first composition initially increases, reaches a maximum and then rapidly decreases. The release of the growth promoters from the coated delayed release formulation is initially delayed over the period that the sustained release formulation releases the growth promoters and until the release reaches the maximum and begins to decline. At about that point in time, the coated formulation, without a burst release of promoters, releases the promoters to provide a composite release of the promoters over the extended period the food animal is in the feedlot. The composite rate of release of the growth promoters of the composition of the present invention is determined by the release rates of the first, the sustained, and the second, the delayed formulations. The sustained, first composition releases the growth promoters upon administration into the food animal. The rate of release of promoters increases sharply, reaches a maximum and then declines. The release of the growth promoters of the second composition is delayed from the time of administration. By adjusting the time at which the second composition release the growth promoters, the composite release is extended over time, the time the food animal is in the feedlot. For example, by adjusting the initial release of the growth promoters of the first composition so that it is sustained over from about 1 day to about 70 days after administration, and the initial release of the second composition so that it is delayed for about 60 days to about 70 days after administration, a composite release extended over about 1 day to about 180 days after administration may be obtained. An extended release of about 200 days after administering the feedlot period for bovines, is attainable by appropriate adjustment of the release characteristics of the sustained and delayed compositions, the uncoated and coated compositions of the growth promoters.

The growth promoting compositions of the present invention are administered to food animals by one of various methods known in the art. Generally, the growth promoting compositions are administered parenterally, typically, subcutaneously as pellets to an inedible member of the animal, by means of a syringe (of sufficient size to accommodate the pellets) or a conventional implant gun, the cartridge thereof being loaded with the pellets containing the sustained and delayed compositions. Administration of the pellets of the growth promoting first and second compositions by simultaneous implantation from the cartridge gun is preferred.

The pellets of the first and second growth promoting compositions may be prepared in various shapes. For implantation by means of an implantation gun, a cylindrical shape is preferred. The length of the cylindrical pellet may vary from about 3 mm to about 6 mm, a length of about 4 mm to about 5 mm being more preferred, a length of about 4.3 mm being most preferred. The diameter of the pellet may vary from about 2 mm to about 4 mm, a diameter of about 2.5 mm to about 3.5 mm also being more preferred. Optionally, the cylindrical pellets may have a beveled edge.

The pellets, preferably cylindrical in shape, as defined above, may contain various amounts of growth promoters and coating levels. For example, the pellets may contain about 16 mg to 24 mg of 17β-acetoxyestra-4,9,11-trien-3-one, preferably about 19 to 21 mg of 17β-acetoxyestra-4,9,11-trien-3-one, more preferably about 20 mg of 17β-acetoxyestra-4,9,11-trien-3-one, and about 2.0 mg to about 6.0 mg of estra-1,3,5(10)-trien-3,17β-diol, preferably about 3.0 mg to about 5.0 mg of estra-1,3,5(10)-trien-3,17β-diol, more preferably either about 2.0 or 4.0 mg of estra-1,3,5(10)-trien-3,17β-diol. Suitable coating levels of DL-lactide-glycolide include on a weight basis about 13 weight percent to about 25 weight percent of the level of 17β-acetoxyestra-4,9,11-trien-3-one and about 11.5 weight percent to about 23.0 weight percent of the level of estra-1,3,5(10)-trien-3,17β-diol.

The pellets, preferably cylindrical in shape, as defined above, may contain various amounts of growth promoters and coating levels. Typically, for example, the pellets may contain about 13 to about 25 weight percent of 17β-acetoxyestra-4,9,11-trien-3-one and about 11.5 to 23.0 weight percent of estra-1,3,5(10)-trien-3,17β-diol.

The desired growth promotion is achieved when the present composition comprising an uncoated composition of growth promoters, the first composition, and a coated composition of growth promoters, the second composition, are administered simultaneously to a food animal at a dose of about 0.75 mg/day/animal to about 1.2 mg/day/animal, a dose of about 0.95 mg/day/animal being preferred to attain the desired weight gain for the period the animal is in the feedlot. These doses are attained when about 8 to about 10 pellets of each composition are administered to the food animal.

The dose level defined above is for the administration of the growth promoters of the composition comprising the first and second compositions of growth promoters to bovines, namely, cows, steers, heifers and calves. For administration to other farm animals, the doses are adjusted accordingly. While the first and second compositions may comprise different growth promoters, i.e. different combinations of the hereinbefore defined compounds and dose levels, it is preferred to administer pellets of the first and second composition comprising the same growth promoters and the same dose levels as determined by the amount of promoters in each pellet and the number of pellets to be administered.

As hereinbefore described the release rates of the growth promoters from the first (uncoated) and second (coated) compositions of the present invention are determined by methods known in the art. In one such determination of release rates (dissolution rates), in vitro, individual pellets of growth promoters 17β-acetoxyestra-4,9,11-trien-3-one and estra-1,3,5(10)-trien-3,17β-diol, uncoated and coated with 75:25-DL-lactide-glycolide copolymer were added to 50 ml of aqueous sodium dodecyl sulfate (5 wt. %) and incubated at 37° C., without agitation. Periodically, samples of the dissolution medium were collected, and the concentration of the growth promoters in the dissolution medium was determined by high performance liquid chromatography. The cummulative release rates of pellets of uncoated 17β-acetoxyestra-4,9,11-trien-3-one and 17β-acetoxyestra-4,9,11-trien-3-one coated with 10.8 wt. % of 75:25 DL-lactide-glycolide polymer (DL-PLG) is shown in Table 1.

TABLE 1

| Elapsed Time days | % Released Uncoated Core | % Released Cores Coated with 75:25 DL-PLG 10.8 wt. % Coating | % Released Cores Coated with 75:25 DL-PLG 19.8 wt. % Coating |
|---|---|---|---|
| 1 | 11.58 | 0.00 | 0.00 |
| 3 | 28.20 | 0.00 | 0.00 |
| 4 | 36.64 | 0.00 | 0.00 |
| 8 | 55.45 | 0.00 | 0.00 |
| 9 | 58.70 | 0.01 | 0.00 |
| 14 | 72.72 | 0.04 | 0.00 |
| 21 | 87.35 | 0.04 | ND |
| 28 | 96.73 | ND | 0.00 |
| 35 | 99.80 | 0.12 | 0.00 |
| 43 | | 0.85 | 0.04 |
| 50 | | 5.04 | 0.94 |
| 57 | | 25.41 | 3.42 |
| 64 | | 42.01 | 10.84 |
| 71 | | 53.07 | ND |

ND—Not determined
DL-PLG refers to the copolymer of DL-lactide-glycolide

The following examples are for illustrative purposes only and are not to be construed as limiting the inventor.

EXAMPLE 1

Granulation of a Composition of 17β-acetoxyestra-4,9,11-trien-3-one and Estra-1,3,5(10)-trien-3,17β-diol with 75:25-DL-lactide-glycolide Copolymer A solution of 52.6 g of 75:25 DL-lactide-glycolide copolymer (Inherent viscosity of 0.67 dL/g in chloroform at 30° C.) in 5210.5 g of acetone was slowly added to a granulation of 1000 g of a mixture of 17β-acetoxy-4,9,11-trien-3-one and estra-1,3,5(10)-trien-3,17β-diol, also containing chloesterol, ehethytylcellulose and magnesium stearate, and was granulated in a 4-L planetary mixer at a slow speed, until the acetone had evaporated. The granulate was ground in a Thomas-Wiley Intermediate Laboratory Mill equipped with a 20 mesh screen and then passed through a sieve to afford a dry granulation of about 60 mesh. The composition of the dry, sieved granulation is shown below, the amounts are in wt. %.

| | |
|---|---|
| 17β-acetoxy-4,9,11-trien-3-one | 59.3 |
| 1,3,5(10)-estra-3,17β-diol | 11.9 |
| Cholesterol | 18.6 |
| Ethyl cellulose | 3.7 |
| Magnesium Stearate | 1.5 |
| 75:25 DL-lactide-glycolide copolymer | 5.0 |

EXAMPLE 2

Tableting of 17β-acetoxyestra-4,9,11-trien-3-one, Estra-1,3,5(10)-trien-3,17β-diol, and 65:25-DL-lactide-glycolide Copolymer Granulation The dried, sieved granulation of Example 1 was tableted on a Stokes-Merrill 900-512-001 Rotary Tablet Press equipped with 3-mm diameter flat-face tooling having a 30°×0.2 mm beveled edge. Fill weight was adjusted to provide pellets with an average weight of about 33 mg, and the compression force was adjusted to provide pellets with an average hardness of about 70 N. After tableting, the length, diameter, and hardness of the tablets were determined on a Vankel VK-200 Tablet Hardness Tester. The amounts of 17β-acetoxyestra-4,9,11-trien-3-one and estra-1,3,5(10)-trien-3,17β-diol of the tablets were determined by extracting individual pellets with ethanol and analyzing the extracts by high performance liquid chromatography. The data are shown in Table 2.

EXAMPLE 3

Coating of the Tablets of 17β-acetoxyestra-4,9,11-trien-3-one and Estra-1,3,5(10)-trien-3,17β-diol with 65:25-DL-lactide-glycolide Copolymer Tablets (40 g as prepared in example 2) and placebo tablets prepared from Avicel PH-101 were charged into the coating chamber of ⅘-in. fluid bed coater (Coating Place, Inc., Verona, Wis.) equipped with a Wurster insert. The tablets were coated with 1.0 wt. % of DL-Lactide-glycolide acid copolymer in acetone solution using the following coating conditions: fluidization air—25–35 SCFM; atomization air—14 psig, 35 SCFH; liquid feed—0.8 mL/min; inlet air temperature—100–107° F.; outlet air temperature—90° F. Coating level was monitored by periodically interrupting the coating process, removing a sample, and measuring weight gain. Samples of coated pellets were removed for testing when the coating level reached approximately 10 wt. % and 20 wt. % of the copolymer. The harness, 17β-acetoxyestra-4,9,11-trien-3-one content and estra-1,3,5(10)-trien-3,17β-diol content of the coated pellets was measured as described above. Coating level was calculated from the change in the percent content of the growth promoters and pellet weight. The data are shown in Table 2.

EXAMPLE 4

Coating of the Tablets of 17β-acetoxyestra-4,9,11-trien-3-one and 1,3,5(10)-trien-3,17β-diol, with 75:25-DL-lacticide-glycolide Acid Copolymer Tablets (40 g prepared in example 2 and 70 g of placebo tablets prepared from Avicel PH-101) were charged into the coating chamber of ⅘-in. fluid bed coater (Coating Place, Inc., Verona, Wis.) equipped with a Wurster insert. The tablets were coated with a 1.0 wt. % 75:25 DL-lactide-glycolide copolymer in acetone solution using the same coating conditions as described in Example 3. Coating level was monitored by periodically interrupting the coating process, removing a sample, and measuring weight gain. Samples of the coated pellets were removed for testing when the coating level has reached approximately 10 wt. % and 20 wt. %. The hardness, 17β-acetoxyestra-4,9,11-trien-3-one content and 1,3,5(10)-estratrien-3,17β-diol content of the coated pellets was measured as described above. Coating level was calculated from the change in the percent content of the actives and pellet weight. The data are shown in Table 2.

TABLE 2

Properties of TBA and E2 Uncoated Pellets and Pellets Coated with Lactide-Glycolide

| Property | Uncoated Pellets | 65:35 DL-lactide-glycolide copolymer coating | 65:35 DL-lactide-glycolide copolymer coating | 75:25 DL-lactide-glycolide copolymer coating | 75:25 DL-lactide-glycolide copolymer coating |
|---|---|---|---|---|---|
| Nominal Coating wt. | | 10% | 20% | 10% | 20% |
| Pellet Wt, mg | 31.2 | 35.3 | 40.2 | 35.5 | 39.9 |
| Pellet Length, mm | 3.96 | 4.22 | 4.35 | 4.17 | 4.26 |
| Pellet Diameter, mm | 2.97 | 3.09 | 3.24 | 3.12 | 3.23 |
| Harness, N | 69.0 | 120.3 | 163.4 | 116.6 | 156.1 |
| TBA Content, mg | 17.2 | 16.9 | 17.4 | 16.7 | 16.8 |
| TBA Content, wt % | 56.0 | 48.3 | 43.2 | 48.8 | 42.5 |
| E2 Content, mg | 3.54 | 3.54 | 3.63 | 3.46 | 3.51 |
| E2 Content, wt % | 11.5 | 10.1 | 9.0 | 10.1 | 8.9 |
| TBA/E Ratio | 4.86 | 4.77 | 4.79 | 4.83 | 4.79 |
| Coating Level (TBA basis), wt % | NA | 13.7 | 22.8 | 12.8 | 24.3 |

TABLE 2-continued

| Property | Uncoated Pellets | 65:35 DL-lactide-glycolide copolymer coating | 65:35 DL-lactide-glycolide copolymer coating | 75:25 DL-lactide-glycolide copolymer coating | 75:25 DL-lactide-glycolide copolymer coating |
|---|---|---|---|---|---|
| | Properties of TBA and E2 Uncoated Pellets and Pellets Coated with Lactide-Glycolide | | | | |
| Coating Level (E2 basis), wt % | NA | 12.2 | 21.7 | 12.2 | 22.6 |
| Coating Level (Wt basis) wt % | NA | 11.6 | 22.4 | 12.1 | 21.8 |

Pellet weight, n = 50; Length, diameter, and hardness, n = 10; TBA and E2 contents, n = 5.
Weight percentage of TBA and E2 were calculated from the individual pellet weights used in the content assay.
TBA refers to 17β-acetoxyestra-4,9,11-trien-3-one
E2 refers to estra-1,3,5(10)-trien-3,17β-diol

We claim:

1. A solid composition for implantation into an animal comprising a first composition comprising at least one compound selected from the group consisting of a compound of the formula

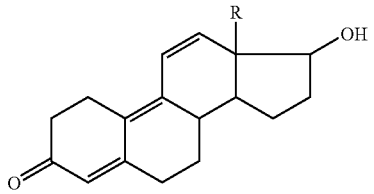

wherein R is loweralkyl, the ester derivatives, geometric isomers, stereoisomers, or optical isomers thereof, a compound of the formula

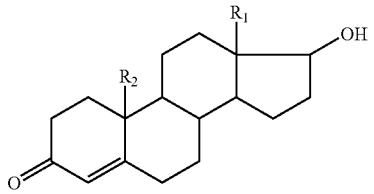

wherein $R_1$ and $R_2$ are loweralkyl, the ester derivatives, geometric isomers, steroisomers, or optical isomers thereof, a compound of the formula

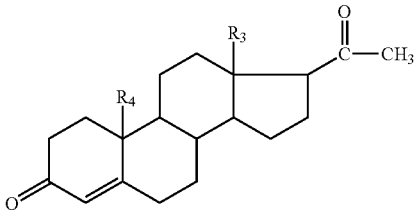

wherein $R_3$ and $R_4$ are loweralkyl, the geometric isomers, stereoisomers, optical isomers thereof, a compound of the formula

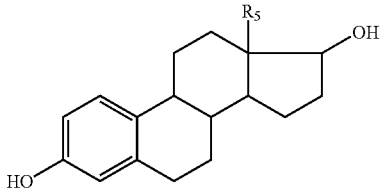

wherein $R_5$ is loweralkyl, the ester derivatives, geometric isomers, stereoisomers, or optical isomers thereof, and a compound of the formula

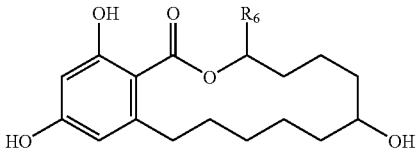

wherein $R_6$ is loweralkyl, the ester derivatives, geometric isomers, stereoisomers, or optical isomers thereof; and a second composition comprising at least one compound selected from the group consisting of a compound of the formula

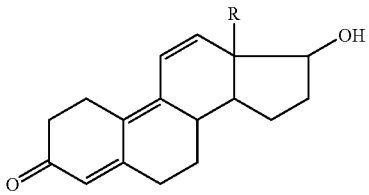

wherein R is loweralkyl, the ester derivatives, geometric isomers, stereoisomers, or optical isomers thereof, a compound of the formula

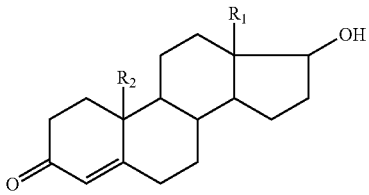

wherein $R_1$ and $R_2$ are loweralkyl, the ester derivatives, geometric isomers, stereoisomers, or optical isomers thereof, a compound of the formula

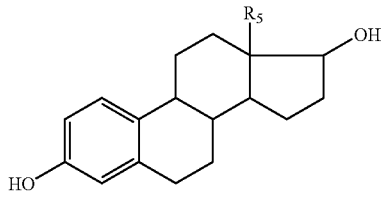

Wherein $R_5$ is loweralkyl, the ester derivatives, geometric isomers, stereoisomers, optical isomers thereof, a compound of the formula

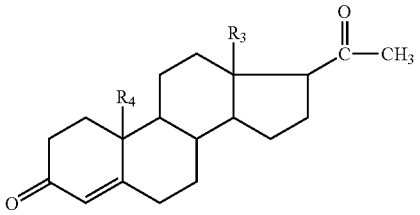

Wherein $R_3$ and $R_4$ are loweralkyl, the geometric isomers, stereoisomers, or optical isomers thereof, and a compound of the formula

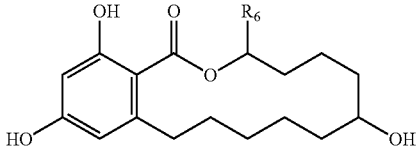

Wherein $R_6$ is loweralkyl, the ester derivatives, geometric isomers, stereoisomers, or optical isomers thereof; and a biodegradable polymer selected from the group consisting of homopolymers and copolymers of γ-butyrolactone, δ-valerolactone, ϵ-caprolactone, glycolide, DL-lactide, L-lactide, glycolic acid, DL-lactic acid, L-lactic acid, and combinations thereof, polydioxanones, polyorthesters, polyanhydrides, polycarbonates, polyesteramides, and polyphosphazines, wherein the second composition is coated on its surface with the biodegradable polymer whereby the release of its comprised compound is a delayed release in an in vivo environment such that the release of the compound of the second composition is delayed until at least about 35 days after placing the composition comprising the first composition and the second composition into an in vivo environment.

2. A composition according to claim 1 wherein R is methyl or the aroyl or alkanoyl ester derivatives thereof.

3. A composition according to claim 1 wherein $R_{1\ and\ R2}$ are methyl or the aroyl or alkanoyl ester derivatives thereof.

4. A composition according to claim 1 wherein $R_3$ and $R_4$ are methyl which is pregn-4-en-3,20-dione.

5. A composition according to claim 1 wherein $R_5$ is methyl or the aroyl or alkanoyl ester derivatives thereof.

6. A composition according to claim 1 wherein $R_6$ is methyl or the aroyl or alkanoly ester derivatives thereof.

7. The composition according to claim 2 wherein the compound is 17β-acetoxyestra-4,9,11-trien-3-one.

8. The composition according to claim 2 wherein the compound is 17β-benzoyloxoxyestra-4,9,11-trien-3-one.

9. The composition according to claim 3 wherein the compound is 17β-propionyloxy-4-androsten-3-one.

10. The composition according to claim 5 wherein the compound is estra-1,3,5(10)-trien-3,17β-diol.

11. The composition according to claim 5 wherein the compound is 17 β-benzoyloxyestra-1,3,5(10)-trien-3-ol.

12. The composition according to claim 6 wherein the compound is 3,4,5,6,9,10,11,12-decahydro-7,14,16-trihydroxy-3-methyl-1H-2-benzoxacyclotetradecin-1-one.

13. A composition according to claim 1 wherein the biodegradable polymer is selected from the group consisting of homopolymers and copolymers of glycolide, DL-lactide, L-lactide, glycolic acid, DL-lactic acid and L-lactic acid and combinations thereof.

14. A composition according to claim 13 wherein the biodegradable polymer is a homopolymer selected from the group consisting of glycolide, DL-lactide and L-lactide.

15. The composition according to claim 13, wherein the biodegradable polymer is a copolymer of DL-lactide and glycolide.

16. The composition according to claim 13, wherein the biodegradable polymer is a copolymer of L-lactide and glycolide.

17. The composition according to claim 14 wherein the biodegradable polymer is a polymer of L-lactide.

18. The composition according to claim 14 wherein the biodegradable polymer is a polymer of DL-lactide.

19. A composition according to claim 13 wherein the homopolymer or copolymer exhibits a glass transition temperature greater than about 40° C.

20. A composition according to claim 13 wherein inherent viscosity of the polymers or copolymers is from about 0.1 dL/g to about 3.5 dL/g.

21. A composition according to claim 20 wherein the inherent viscosity is from about 0.3 dL/g to about 1.5 dL/g.

22. A composition according to claim 13 wherein the ratio of lactide units to glycolide units is from about 90:10 to about 50:50.

23. A composition according to claim 22 wherein the ratio of lactide units to glycolide units is from about 75:25 to about 60:40.

24. A weight gain composition comprising an excipient and as the active ingredient, a weight gain effective amount of a composition according to claim 1.

25. The composition according the claim 1, wherein the first composition and the second composition are each in the form of a pellet and wherein the length of the pellet is from about 3 mm to about 6 mm.

26. The composition according to claim 25 wherein the length of the pellet is from about 4 mm to about 5 mm.

27. The composition according to claim 26 wherein the length of the pellet is about 4.3 mm.

28. The composition according to claim 1, wherein the first composition and the second composition are each in the form of a pellet and wherein the diameter of the pellet is from about 2 mm to about 4 mm.

29. The composition according to claim 28 wherein the diameter of the pellet is from about 2.5 mm to about 3.5 mm.

30. The composition according to claim 29 wherein the diameter of the pellet is about 3.2 mm.

31. The composition according to claim 30 wherein the length of the pellet is about 4.3 mm and the diameter is about 3.2 mm.

32. The composition according to claim 1, wherein the first composition and the second composition are each in the form of a pellet and wherein the pellet contains from about 16 mg to about 24 mg of 17 β-acetoxyestra-4,9,11-trien-3-one.

33. The composition according to claim 32 wherein the pellet contains from about 19 mg to about 21 mg of 17 β-acetoxyestra-4,9,11-trien-3-one.

34. The composition according to claim 33 wherein the pellet contains about 20 mg of 17 β-acetoxyestra-4,9,11-trien-3-one.

35. The composition according to claim 34 wherein the pellet contains from about 2.0 mg to about 6.0 mg of estra-1,3,5(10)-trien-3,17 β-diol.

36. The composition according to claim 35 wherein the pellet contains from about 3.0 mg to about 5.0 mg of estra-1,3,5(10)-trien-3,17 β-diol.

37. The composition according to claim 36 wherein the pellet contains about 4.0 mg of estra-1,3,5(10)-trien-3,17 β-diol.

38. The solid composition for implantation according to claim 1, wherein the release of the at least one compound of the second composition is delayed until at least about 45 days after placing the composition into an in vivo environment.

39. The solid composition for implantation according to claim 1, wherein the release of the at least one compound of the second composition is delayed until at least about 55 days after placing the composition into an in vivo environment.

40. The solid composition for implantation according to claim 1, wherein the release of the at least one compound of the second composition is delayed until at least about 60 days after placing the composition into an in vivo environment.

41. The solid composition for implantation according to claim 1, wherein the release of the at least one compound of the second composition is delayed until at least about 70 days after placing the composition into an in vivo environment.

42. A method of promoting weight gain in a farm animal comprising a single administration to a farm animal of a weight gain effective amount of a solid composition according to claim 1, wherein the at least one compound of the first composition is available immediately on administration and the at least one compound of the second composition is available at a predetermined time controlled by the biodegradable polymer with which it is coated, said second composition not being available for at least about 35 days after being placed into an in vivo environment.

43. The method of claim 42, wherein the second composition is not available for at least about 45 days after being placed into an in vivo environment.

44. The method of claim 42, wherein the second composition is not available for at least about 55 days after being placed into an in vivo environment.

45. The method of claim 42, wherein the second composition is not available for at least about 60 days after being placed into an in vivo environment.

46. The method of claim 42, wherein the second composition is not available for at least about 70 days after being placed into an in vivo environment.

*47. A solid composition for implantation into an animal comprising two compositions, wherein the first composition comprises at least one compound selected from the group consisting of a compound of the formula*

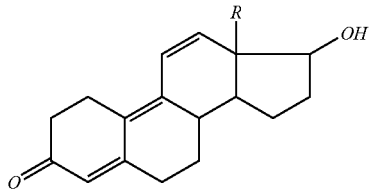

*wherein R is loweralkyl, the ester derivatives, geometric isomers, stereoismers, or optical isomers thereof, a compound of the formula*

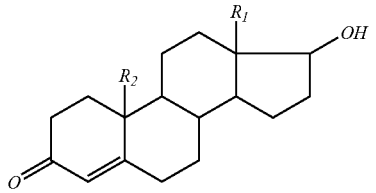

*wherein $R_1$ and $R_2$ are loweralkyl, the ester derivatives, geometric isomers, stereoisomers, or optical isomers thereof, a compound of the formula*

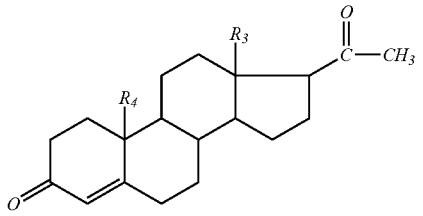

*wherein $R_3$ and $R_4$ are loweralkyl, the geometric isomers, stereoisomers, optical isomers thereof, a compound of the formula*

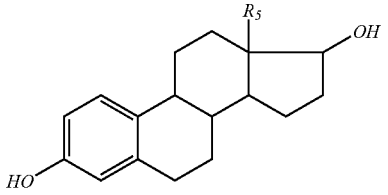

*wherein $R_5$ is loweralkyl, the ester derivatives, geometric isomers, stereoisomers, or optical isomers thereof, and a compound of the formula*

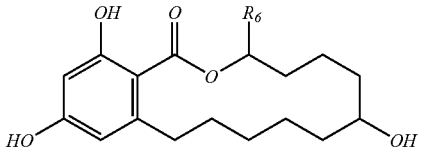

*wherein $R_6$ is loweralkyl, the ester derivatives, geometric isomers, stereoisomers, or optical isomers thereof; and wherein the second composition, comprising at least one compound selected from the group consisting of a compound of the formula*

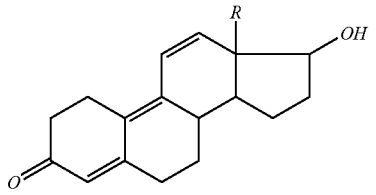

*wherein R is loweralkyl, the ester derivatives, geometric isomers, stereoisomers, or optical isomers thereof, a compound of the formula*

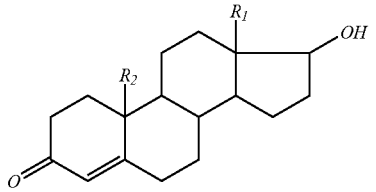

*wherein $R_1$ and $R_2$ are loweralkyl, the ester derivatives, geometric isomers, stereoisomers, or optical isomers thereof, a compound of the formula*

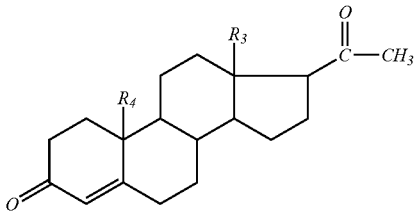

*wherein $R_3$ and $R_4$ are loweralkyl, the geometric isomers, stereoisomers, optical isomers thereof, a compound of the formula*

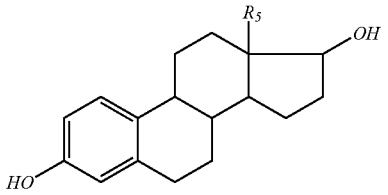

*wherein $R_5$ is lower alkyl, the ester derivatives, geometric isomers, stereoisomers, or optical isomers thereof, and a compound of the formula*

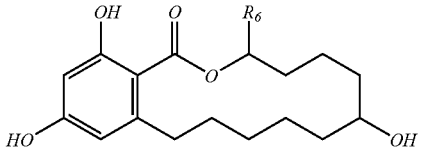

*wherein $R_6$ is loweralkyl, the ester derivatives, geometric isomers, stereoisomers, or optical isomers thereof; wherein the second composition is coated on its surface with a biodegradable polymer whereby its release is delayed at least 35 days in an in-vivo environment.*

*48. A method of promoting weight gain in a farm animal comprising a single administration to a farm animal of a weight gain effective amount of a solid composition according to claim 47, wherein the at least one compound of the first composition is available immediately on administration and the availability of at least one compound of the second composition is essentially delayed for at least 35 days.*

*49. The composition of claim 25, wherein the pellet has a beveled edge.*

*50. The composition of claim 28, wherein the pellet has a beveled edge.*

*51. The composition of claim 47, wherein the second composition further comprises a biodegradable polymer.*

*52. The composition of claim 1, wherein the first composition and the second composition further comprise a biodegradable polymer.*

*53. The composition of claim 47, wherein the first composition and the second composition further comprise a biodegradable polymer.*

* * * * *